United States Patent [19]

Defaye et al.

[11] Patent Number: 4,737,584
[45] Date of Patent: Apr. 12, 1988

[54] PROCESS FOR CYCLO-DEHYDRATING KETOSES

[75] Inventors: Jacques Defaye; Andrée Gadelle, both of Saint Ismier; Christian Pedersen, Virum, all of France

[73] Assignee: Beghin-Say S.A., Thumeries, France

[21] Appl. No.: 723,965

[22] PCT Filed: Aug. 8, 1984

[86] PCT No.: PCT/FR84/00186
§ 371 Date: Apr. 5, 1985
§ 102(e) Date: Apr. 5, 1985

[87] PCT Pub. No.: WO85/00814
PCT Pub. Date: Feb. 28, 1985

[30] Foreign Application Priority Data

Aug. 8, 1983 [FR] France .............................. 83 13031
Aug. 8, 1983 [FR] France .............................. 83 13032

[51] Int. Cl.$^4$ .................. C08B 37/18; C07H 15/00; C07H 15/24; C07H 17/00
[52] U.S. Cl. ................... 536/18.1; 536/18.5; 536/124
[58] Field of Search ................ 536/18.1, 124, 18.5

[56] References Cited
PUBLICATIONS

Chemical Abstracts, vol. 90, No. 21, May 21, 1979, abstract 90: 168,844k.
Chemical Abstracts, vol. 85, No. 6, Aug. 9, 1976, abstract 85: 34,931z.

*Primary Examiner*—Ronald W. Griffin
*Attorney, Agent, or Firm*—A. W. Breiner

[57] ABSTRACT

The invention concerns a process for dehydrating glucides and applicable to those glucides of which the molecule includes at least one ketose type group, being characterized in that the glucide is made to react without addition of water with a hydrogen halide, whereupon the hydrogen halide is eliminated by evaporation in order to collect the formed disaccharide anhydride.

The invention also relates to novel products characterized by essentially consisting of saccharide anhydrides of which the molecule includes two saccharide cycles linked to each other by two acetal bonds included in a dioxane cycle. As a rule at least one of the saccharide cycles is that of fructose (and may be substituted), and this cycle is linked by a spirane bond to the dioxane cycle.

Product application as food additives.

9 Claims, No Drawings

PROCESS FOR CYCLO-DEHYDRATING KETOSES

The object of the invention is a process for cyclodehydrating ketoses, the obtained products, and their use as food additives.

More particularly, the invention concerns the field of substitutes for food sugars.

Products substituting for food sugars have already long been sought in order to avoid the vexatious consequences of excessive consumption of these food sugars.

For instance, it has already been suggested to use products which while evincing a more or less pronounced sweetening effect are also characterized by not being metabolized by the human organism. These products also are termed "non-caloric food sugars." The sizeable sweetening effect of a dipeptide, namely the methylester of the alpha-aspartyl phenylanilin (or aspartame), described in particular in French Pat. No. 1,577,545 has already been long known.

One of the problems related to using aspartame as a sweetener is that in the light of its high sweetening effect, this compound can only be used in small amounts. Furthermore, it is present only in the crystalline form. To make it acceptable to the consumer, it must therefore be associated with a neutral excipient.

The purpose of the invention, therefore, is to propose glucide analogues of which some are novel products per se and which due to their features of being not assimilated by the organism are capable of entering either alone or in mixture the composition of a non-caloric food sugar, or which can be used as an excipient for a conventional or synthesized sweetener so as to make possible an association with a sweetening power which is equal or higher, but always non-caloric.

Another purpose of the invention is to propose a process for advantageously synthesizing these products.

The process for cyclo-dehydrating glucides of which the molecule includes at least one ketose-type group is characterized in that without adding water, the glucide is made to react with a hydrogen halide acting as the glucide solvent, and in that the hydrogen halide is eliminated in a dry manner.

The hydrogen halides are selected from the hydrogen iodides, bromides, chlorides, or fluorides. Among these, hydrogen chloride and hydrogen fluoride result in substantially higher yields in dehydrated compounds since the reaction in the presence of hydrogen bromide or iodide results in a high proportion of waste residues.

Advantageously hydrogen chloride or fluoride will be used because these halides allow making products at excellent yields. Hydrogen fluoride is the preferred halide because it results in practically quantitative yields.

The glucides of which the molecule includes at least one ketose-type group can be ketotetroses, ketopentoses, or ketohexoses. They may be in monomeric or polymeric form, the latter expression including the dimers.

Advantageously the glucides with a ketopentose group are selected from xylulose or one of its polymers.

The glucides with a ketohexose group are the preferred glucides for implementing the process of the invention. Among these are illustratively fructose, inulin, and sorbose.

The invention further includes the above-cited glucides of which the molecules comprise one of or more substitutents of ether, ester, acetal or other type, and in a position such as not to hamper the cyclo-dehydration reaction.

Of all of these compounds, those glucides are preferred wherein at least one of the saccharide cycles is fructose is sorbose.

The reaction takes placed without added water. This does not mean it takes place anhydrously because–a dehydration process being involved–water is automatically being formed as the reaction proceeds toward the dehydrated compounds. Additionally, the initial products may be partly hydrated.

However, the proportion of water at the end of the reaction may not exceed 10% by weight of the final reaction mixture in order not to decrease the yield in dehydrated compounds.

However, in a preferred variation, the halide is introduced dry. Similarly, the sugar to be reacted is previously dried so it shall no longer contain any water except the water of crystallization.

The glucide may be made to contact the halide in a variety of ways. Thus, the halide may be circulated in the gaseous state, under pressure, or entrained while diluted in an inert carrier gas such as nitrogen or sulfur dioxide.

When the invention was implemented, the process effectiveness appeared to be directly related to the dissolution of the processed glucide in the hydrogen halide. Preferably, therefore, the glucide is dissolved in the halide in the liquid state and advantageously the glucide shall be completely dissolved in the halide. The reaction temperature advantageously is between $-20°$ C. and $+25°$ C. Thereafter the halide is eliminated by any suitable means, for instance by evaporation in particular.

The reaction may be partial, but nevertheless results in products of which the application is explained below.

Preferably the hydrogen halide is made to react in molar excess with respect to the number of ketose monosaccharide equivalents.

Advantageously the molar ratio of hydrogen halide to ketose monosaccharide equivalents is between 5 and 100, and better yet between 6 and 50.

The process of the invention results in saccharide dianhydrides which are easily isolated by crystallization; and, furthermore, they are obtained in the pure state at very high yields. Be it noted too that regardless of the initial glucide, the reaction appears to favor forming the ketose dimer in the dianhydrides of the invention.

Another object of the present invention are the products obtained by the above-described process.

Another object of the invention is the novel products consisting of saccharide anhydrides which are characterized in being essentially formed by saccharide dianhydrides of which the molecule comprises two saccharide cycles linked to each other by two acetal bonds included in a dioxane cycle.

Preferably at least one of the saccharide cycles is a ketose type cycle, in particular that of fructose, and this cycle is linked to the dioxane cycle by a spirane bond.

It is known that the ketoses are glucides which, contrary to the case of the aldoses, include at least one ketone function.

However, it must be borne in mind that the fructose or other ketose cycle may be substituted. In other words, in the above expression, not only are we including the fructose proper, but also the homologous ketoses, the isomers with a configuration like the sorbose, and the ketoses of which the molecule comprises one or more substituents of the ether, ester, acetal or other type.

Preferably the anhydrides consist in part of D-fructose dianhydrides.

Preferably the anhydrides essentially consist of a mixture of dianhydrides of di-D-fructopyranose and/or fructofuranose and fructopyranose.

More particularly, the invention includes the following novel products:
di-alpha-d-fructopyranose 1,2':2,1' dianhydride
beta-D-fructofuranose beta-D-fructopyranose 1,2':2,1' dianhydride
beta-D-fructofuranose alpha-D-fructopyranose 2,1':3,2' dianhydride
sorbose dianhydride.

Another object of the invention is the application of the above-described products possibly obtained by the previously described process as food additives.

Remarkably the products of the invention are both non-toxic and non-hydrolyzing, whereby they constitute non-assimilated foods. Due to their structure, moreover, it is clear that even if they were destroyed within the organism, their hydrolysis would only result in non-toxic products consisting of sugar molecules, in particular fructose. The presence of these products in food sugar allows decreasing the caloric power of sugar and of the foods into which they are incorporated.

The products of the invention can be prepared by dehydrating known sugars. If, for instance, saccharose is involved, even a partial dehydration results in a less caloric sugar than the initial product. Therefore, another object of the invention is a process for treating sugars to decrease their caloric power and characterized essentially by providing at least a partial dehydration of the sugar in conditions leading to the formation of acetal bonds between the saccharide cycles.

Furthermore, some of these products provide a sweet taste while others are wholly tasteless (neutral taste). They are crystallized and water-soluble. Therefore, they can be advantageously combined with a well-known sweetener such as aspartame, acesulfam, saccharin, or the like.

Accordingly, another object of the invention is a food product containing 1% to 10% by weight of aspartame or the like, and 90% to 99% of one of the compounds of the invention.

The invention is illustrated below by particular implementing examples.

EXAMPLE I 5 g of inulin from Sigma dahlia tubers, cooled to 0° C., receive 10 ml of hydrogen fluoride which also was cooled. The solution is allowed to stand at room temperature (20° C.) for about 45 minutes, whereupon the hydrogen fluoride is evaporated by pressure reduction or by being entrained in a gas flow. The residue is then reprocessed with ether.

4.8 g of a product consisting of D-fructose anhydrides and identified chromatographically in the gaseous phase as methylated products are recovered. The product appears being formed by a mixture including in percent by weight of the total weight of the following:
12% of (1):di-alpha-D-fructopyranose 1,2':2,1' dianhydride
  Melting point: 293°–295° C.
  Rotation $[\alpha]_D$: −46°.

14% of (2):di-beta-D-fructopyranose 1,2':2,1' dianhydride
  Melting point: 279° C.
  Rotation $[\alpha]_D$: −300°.
45% of (3):alpha-D-fructofuranose alpha-D-fructopyranose 1,2':2,1' dianhydride
  Melting point: 258° C.
  Rotation $[\alpha]_D$: −39°.
4% of (4):beta-D-fructofuranose beta-D-fructopyranose 1,2':2,1' dianhydride
  Melting point: 240° C.
  Rotation $[\alpha]_D$: −182°.
18% of (5) : beta-D-fructofuranose alpha-D-fructopyranose 2,1':3,2' dianhydride
  Melting point: 206° C.
  Rotation $[\alpha]_D$: −58.5°.

EXAMPLE II 20 g of D-fructose are treated with 20 ml of hydrogen fluoride (HF) at −10° C. for three minutes, then the hydrogen fluoride is evaporated using air at reduced pressure. Cooled diethylether is added to the residue. The precipitate is decanted and reprocessed several times with diethylether, then decanted and filtered.

18.4 g of a product consisting of a mixture of D-fructose dianhydrides, chromatographically identified in the gaseous phase and denoted as in Example I are recovered. In percent of weight with respect to the total weight, the mixture includes:
  14% of (1)
  20% of (2)
  58% of (3)
  7% of (5)

By varying the conditions, that is the amount of HF (1 ml per 1 g as a minimum to 10 ml per 1 g), the temperature (−10° C. to +20° C.) and the time (from 2 minutes to 5 hours), sugars are obtained which essentially consist of the same five compounds already identified in Example I, though in different proportions, within the distributions below:
  from 10% to 20% for (1)
  from 10% to 20% for (2)
  from 30% to 60% for (3)
  from 4% to 8% for (4)
  from 10% to 30% for (5)

EXAMPLE III 18.4 g of the mixture obtained in Example II (first section) are processed with 20 ml of methanol and made to crystallize. The compounds (1) and (2) are directly recovered (4 g).

The dried mother liquors solely consist of the derivatives (3), (4), and (5). The derivative (3) is the main derivative (40%) of the mixture, and is crystallized by adding seed-forming crystals to the mother liquors reprocessed in ethanol. The product purity is about 98%.

Proceeding in the same manner but using a mixture obtained per Example II, under different conditions, this compound (3) is obtained with a yield of 60%.

EXAMPLE IV

Proceeding in cold conditions as in Example I, 10 g of L-sorbose are treated with 10 ml of HF for one minute at −10° C. The product is precipitated with diethylether. The amount recovered is 9.2 g. This is a mixture of several compounds identified as being L-sorbose dianhydrides. The following compounds are sequentially identified chromatographically in the gaseous phase and by carbon nuclear magnetic resonance:
di-alpha-L-sorbopyranose 1,2':2,1' dianhydride
di-beta-L-sorbopyranose 1,2':2,1' dianhydride
alpha-L-sorbofuranose alpha-L-sorbopyranose 1,2':2,1' dianhydride
alpha-L-sorbofuranose beta-L-sorbopyranose 1,2':2,1' dianhydride
alpha-L-sorbofuranose beta-L-sorbopyranose 1,2':3,1' dianhydride The products can be isolated in the same manner as for D-fructose (Example II) by adding methanol, then ethanol.

EXAMPLE V 5 g of saccharose are mixed with 10 ml of hydrogen fluoride at 0° C. The mixture is allowed to react for 2.5 minutes, then the product is precipitated with ether. 4.8 g are recovered.

The mixture so obtained contains glucosyl fluoride (analyzed using 13C nuclear magnetic resonance). Study of the methylated products shows the presence of D-fructose dianhydrides; the five compounds defined in Example I are present.

In quantitative terms, the mixture contains 18% of D-fructose in the form of dianhydrides.

Due to treatment with hydrogen fluoride, the initial saccharose, therefore, has become enzymatically non-hydrolyzing and its caloric power is decreased.

EXAMPLE VI

The products from the Examples I through IV are checked for the properties allowing to use them as saccharose substitutes in foodstuffs.

These products are non-toxic. They are all water-soluble, and the syrups prepared vary in viscosity as a function of concentration the way common sugar does.

Illustratively the last mixture of D-fructose anhydrides prepared per Example II is not hydrolyzed by 0.01N HCl at 37° C. for 0.5 hour. As a rule, the hydrolysis rate at 20° C. and in the presence of 1N sulfuric acid of the various compounds is about 1,000 times less than that of saccharose.

Furthermore, when a partly treated mixture containing dianhydrides is subjected to fermentation by brewer's yeast, the untransformed sugars will be sensitive to the yeast and can be eliminated, whereas the dianhydrides of the invention are left unaffected.

EXAMPLE VIII 5 g of xylulose syrup are treated with 10 ml of liquid hydrogen fluoride for 2 minutes at −10° C. Ethylether is then added to this solution. Following decanting, 4.5 g of the products below are collected:
di-alpha-D-xylulofuranoside 1,2'-2,1' dianhydride
di-beta-D-xylulofuranoside 1,2'-2,1' dianhydride
alpha-D-xylulofuranoside beta-D-xylulofuranoside 1,2'-2,1' dianhydride
alpha-D-xylulofuranoside beta-D-xylulofuranoside 1,2'-3,1' dianhydride.

We claim:

1. A process for cyclo-dehydrating glucides of which the molecule includes at least one ketose type group, characterized in that this glucide is made to react without added water with hydrogen fluoride used as a solvent for the glucide, whereupon the hydrogen fluoride is eliminated in a dry manner.

2. Process per claim 1, characterized in that the initial glucide is selected from fructose, saccharose, inulin, and sorbose.

3. Process per claim 1, characterized in that the molar ratio of hydrogen fluoride to said ketose is between 5 and 100.

4. Process per claim 1, characterized by being carried out in such conditions that the amount of water present in the reaction medium prior to eliminating the hydrogen fluoride is less than 10% by weight.

5. Process per claim 1, characterized in that the reaction is carried out with the hydrogen fluoride in the liquid state.

6. Process per claim 5, characterized in that the temperature of the reaction medium is between −20° C. and +25° C.

7. Process per claim 5, characterized by the hydrogen fluoride being eliminated by evaporation following the reaction.

8. Process per claim 1, characterized in that the molar ratio of hydrogen fluoride to said ketose is between 6 and 50.

9. Glucide anhydrides obtained by the process of claim 1.

* * * * *